United States Patent

Hoctor et al.

(10) Patent No.: US 6,607,489 B2
(45) Date of Patent: Aug. 19, 2003

(54) FOCUS CORRECTION FOR ULTRASOUND IMAGING THROUGH MAMMOGRAPHY COMPRESSION PLATE

(75) Inventors: Ralph Thomas Hoctor, Saratoga Springs, NY (US); Kai Erik Thomenius, Clifton Park, NY (US)

(73) Assignee: General Electric Company, Niskayuna, NY (US)

( * ) Notice: Subject to any disclaimer, the term of this patent is extended or adjusted under 35 U.S.C. 154(b) by 0 days.

(21) Appl. No.: 09/826,149

(22) Filed: Apr. 5, 2001

(65) Prior Publication Data

US 2002/0173722 A1 Nov. 21, 2002

(51) Int. Cl.$^7$ ................................. A61B 8/00
(52) U.S. Cl. ................. 600/443; 600/448; 600/444
(58) Field of Search .................. 600/407–472

(56) References Cited

U.S. PATENT DOCUMENTS

| | | | | |
|---|---|---|---|---|
| 4,130,112 A | * | 12/1978 | Frazer | 600/448 |
| 4,669,311 A | * | 6/1987 | McKinnon | 73/598 |
| 4,852,577 A | * | 8/1989 | Smith et al. | 600/443 |
| 5,268,876 A | * | 12/1993 | Rachlin | 367/7 |
| 5,433,202 A | * | 7/1995 | Mitchell et al. | 600/444 |
| 5,479,927 A | | 1/1996 | Shmulewitz | |
| 5,603,326 A | * | 2/1997 | Richter | 600/443 |
| 5,605,154 A | * | 2/1997 | Ries et al. | 600/444 |
| 5,640,956 A | | 6/1997 | Getzinger et al. | |
| 5,655,535 A | * | 8/1997 | Friemel et al. | 600/443 |
| 5,664,573 A | * | 9/1997 | Shmulewitz | 600/445 |
| 5,673,699 A | * | 10/1997 | Trahey et al. | 600/447 |
| 5,938,613 A | * | 8/1999 | Shmulewitz | 600/461 |
| 6,041,248 A | * | 3/2000 | Wang | 600/407 |

* cited by examiner

Primary Examiner—Marvin M. Lateef
Assistant Examiner—William C. Jung
(74) Attorney, Agent, or Firm—Jean K. Testa; Patrick K. Patnode

(57) ABSTRACT

A coherent imaging system includes a transmitter and a receive beamformer which are programmed with transmit and receive time delays, respectively, that take into account time-of-flight errors caused by an intervening mammography compression plate between the biological tissue being imaged and a phased array of ultrasonic transducer elements. A simple ray-tracing method is utilized to adjust the transmit and receive time delays according to compression plate thickness and speed of ultrasound propagation to mitigate spherical aberration due to the compression plate.

20 Claims, 4 Drawing Sheets

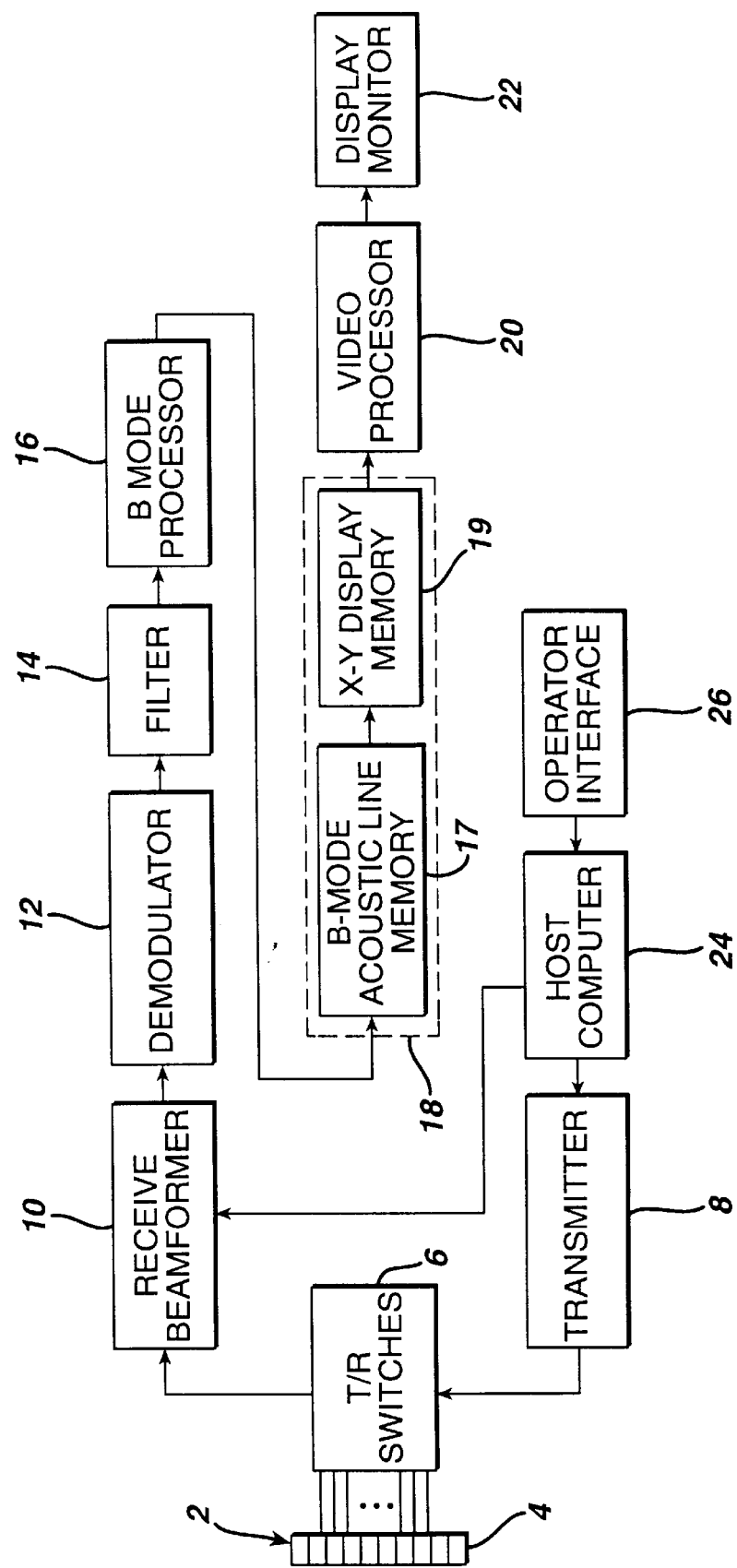

FOCUS CORRECTION FOR ULTRASOUND IMAGING THROUGH MAMMOGRAPHY COMPRESSION PLATE

BACKGROUND OF THE INVENTION

This invention relates to coherent imaging methods applicable to a phased array ultrasonic transducer and, more particularly, to beamforming techniques for use in ultrasound imaging systems.

X-ray mammography is presently the primary screening procedure for detection of breast lesions. Sonography is often used to confirm screening results and also used as a complementary method when X-ray mammography has failed to confirm the results of a manual examination. Often, two separate imaging procedures are required for a single patient, which is inconvenient and may even delay diagnosis.

Hand-held ultrasound transducer probes have been used in free-hand examinations to complement X-ray mammography. A drawback of such freehand examinations, when used to supplement mammography, is the inability to provide geometric registration between the mammogram and ultrasound images. This lack of registration makes it difficult to relate what is seen in the ultrasound image to what is seen in the mammogram. Furthermore, the three dimensional shape of the lesions and the increased vascularity associated with carcinoma make volumetric spatial registration of the ultrasonic data with a mammogram desirable. In light of the foregoing, the development of equipment capable of performing both imaging exams, i.e., X-ray and ultrasound, at the same time and in registration would be an advance.

U.S. Pat. No. 5,479,927 describes apparatus that combines mammography equipment with an ultrasonic transducer to generate ultrasonic images of the internal structure of breast tissue that are in geometric registration with a mammogram. The apparatus includes a radiolucent and sonolucent compression plate. Either before or after the X-ray exposure, a carriage-mounted ultrasound transducer is translated in increments across the compression plate to generate a plurality of sectional views of the breast tissue. The X-ray and ultrasound images produced by this sono-mammography apparatus are ideally in geometric registration. Those images may in turn be processed by a conventional microprocessor-based workstation to provide holographic views of the internal features of a patient's breast.

X-ray mammography images are typically obtained using a plastic plate to compress the breast. The compression plates used in X-ray mammography were historically made of polycarbonates because of their tensile strength and transparency to X-ray. These materials are acoustically opaque. Because of their high densities, most other materials potentially useful for the compression plates in mammography equipment have relatively high attenuation and reflection coefficients for acoustic wave energy. U.S. Pat. No. 5,479,927 describes use of a compression plate made of a high-performance acoustically transparent (sonolucent) and X-ray transparent (radiolucent) film which is sufficiently rigid to serve as a compression plate at a thickness of about 25 micron (1 mil).

Since it would be advantageous to have images that are directly comparable for the X-ray and ultrasound modalities, it would be desirable to form the ultrasound image through the compression plate. However, since acoustic propagation within the compression plate is substantially different than in water or the coupling gel, refraction effects on the waves emitted from the transducer elements of a phased array would severely corrupt the beamforming process of an ultrasound imager, since the beamforming time delays assume a constant velocity of 1,540 m/sec. (meters per second).

Conventional ultrasound imaging systems comprise an array of ultrasonic transducer elements which are used to transmit an ultrasound beam and receive the reflected beam from the object being studied. Such scanning comprises a series of measurements in which the focused ultrasonic wave is transmitted, the system switches to receive mode after a short time interval, and the reflected ultrasonic wave is received, beamformed and processed for display. Typically, transmission and reception are focused in the same direction during each measurement to acquire data from a series of points along an acoustic beam or scan line. The receiver is dynamically focused at a succession of ranges along the scan line as the reflected ultrasonic waves are received.

For ultrasound imaging, the array typically has a multiplicity of transducer elements arranged in one or more rows and driven with separate voltages. By selecting the time delay (or phase) and amplitude of the applied voltages, the individual transducer elements in a given row can be controlled to produce ultrasonic waves which combine to form a net ultrasonic wave that travels along a preferred beam vector direction and is focused at a selected point along the beam. The beamforming parameters of each of the firings may be varied to provide a change in maximum focus or otherwise change the content of the received data for each firing, e.g., by transmitting successive beams along the same scan line with the focal point of each beam being shifted relative to the focal point of the previous beam. For a steered array, by changing the time delays and amplitudes of the applied voltages, the beam with its focal point can be moved in a plane to scan the object. For a linear array, a focused beam directed normal to the array is scanned across the object by translating the aperture across the array from one firing to the next.

The same principles apply when the transducer probe is employed to receive the reflected sound in a receive mode. The voltages produced at the receiving transducer elements are summed so that the net signal is indicative of the ultrasound reflected from a single focal point in the object. As with the transmission mode, this focused reception of the ultrasonic energy is achieved by imparting separate time delay (and/or phase shifts) and gains to the signal from each receiving transducer element.

In a conventional ultrasound imager, the transmit and receive time delays are pre-computed and then stored in memory. These time delays are computed to compensate for time-of-flight from the center of the array element to the focal point, under the assumption of a uniform medium with a speed of sound of 1,540 m/sec. The coherence requirements for beamforming are quite demanding. Typically only about ¼ cycle of error (peak to peak) can be tolerated before there is significant processing loss in signal and reduction in the resolution of the point spread function. For typical high-quality imaging the total error allowed is about ¹⁄₁₆ of a cycle.

The time delays needed for coherent beamforming can be determined using the geometrical theory of diffraction in conjunction with ray tracing. The receiving array is attempting to dynamically focus on a moving wave packet that is traveling out from the array along a scan line anchored at the phase center with an angle θ and at a constant speed. As the wave packet moves out, it illuminates reflecting elements that radiate a multiplicity of spherical waves back to the array. The array itself consists of discrete receiving elements that are arrayed in space according to the geometry of the transducer (e.g., linear arrays, curved arrays, two-dimensional arrays).

The basic nature of the diffraction involved in phased array beamforming can be reduced to a triangle. The hypotenuse of the triangle is determined by the path of a beam leaving the array at the phase center and traveling out at angle θ. The base of the triangle is the straight line distance between the phase center and the i-th transducer element in the array. The third side of the triangle is the distance from a point along the beam to the i-th element. As the wave packet moves out, its range R changes linearly with time according to the speed of propagation in the medium. At any instant, a reflection from a scatterer along the beam can radiate a spherical wave back to a receiving element. The triangle represents the fundamental geometry of a transducer. The distance from the phase center of the array to the field point (the location of the scatterer) is R and the location of the field point is easily given using sine and cosine of θ. To compute the distance from the field point to the i-th transducer element in the array, one must first calculate the values of the coordinates of the field point. The propagation distance is a function of the location of the field point and the location of the i-th element.

The foregoing triangulation method for computing beamformer time delays works well in the absence of an intervening layer having a speed of ultrasound propagation different from that of the biological tissue being imaged. However, since the speed of sound in a plastic mammography compression plate is typically much higher than the nominal speed of sound conventionally used to pre-compute the focusing delays of the ultrasound device, defocusing of the ultrasound beam will result. In order to produce a focused beam under these conditions, the transmit and receive time delays must be re-computed.

Passing a focused beam through a flat plate having different propagation speed from that of the surrounding medium need not cause noticeable defocusing. If the beam originates from a small aperture, or if the plate is thin (as is true case for an array with a thin plastic lens on its front face), then the effect of the plate is only to change the focal length by an amount related to the plate thickness. (In this instance, the flat plate can also be used to displace the focus from side to side, as is done in telescopes.) However, if the aperture is large (that is, if the maximum slope angle of the beam to the focus is large) or if the plate is thick, then spherical aberration results. Because of the short focal lengths and relatively large transducer apertures in an ultrasound imaging system, this problem will arise whenever a system operator attempts to acquire an ultrasound image of a compressed breast through a plastic compression plate. In that event, a suitable correction must be applied in order to form an in-focus image.

BRIEF SUMMARY OF THE INVENTION

In a preferred embodiment of the invention, a method of imaging tissue comprises the steps of: compressing the tissue by pressing a plastic plate against the tissue; holding the compression plate in a fixed position; acquiring an X-ray image of the compressed tissue through the compression plate in the held position; acquiring an ultrasound image of the compressed tissue through the compression plate in the same held position; and registering the X-ray and ultrasound images.

The invention enables an ultrasound imaging system to acquire an image of tissue through a plastic plate. In a preferred embodiment, a beamformer is programmed with pre-stored transmit and receive time delays which have been computed to correct for the effects of refraction caused by an intervening plastic mammography compression plate of an X-ray mammography unit. This correction enables acquisition of an in-focus ultrasound image taken under the same conditions as an X-ray mammography image. Since the two images are formed from the same source under the same conditions, they can be registered, and their information compared on a point-by-point basis.

To eliminate the spherical aberration due to an intervening layer of plastic between the beamformer and the biological tissue being imaged, a ray tracing method is substituted for the conventional triangulation method in the computation of beamformer time delays. For the purpose of computing time delays, this approach uses a ray-tracing method where the refraction occurs at the interface of the plastic layer and adjacent tissue.

BRIEF DESCRIPTION OF THE DRAWINGS

FIG. 3 is a block diagram of one type of ultrasound imaging system which can be coupled to the ultrasound transducer array of a sonomammography apparatus and programmed in accordance with the preferred embodiment of the invention.

DETAILED DESCRIPTION OF THE INVENTION

Figure 1:
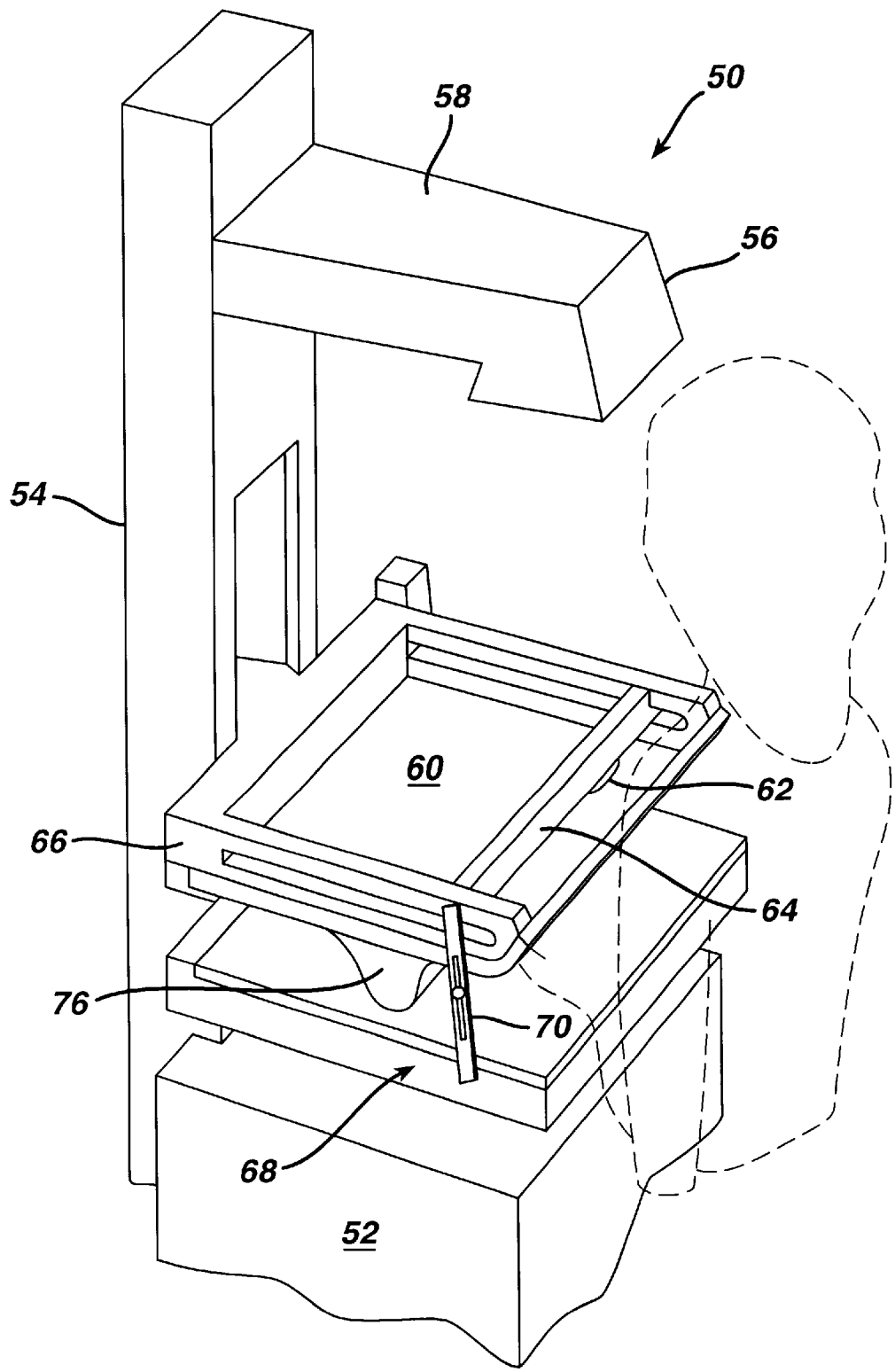
FIG. 1 is a schematic perspective view of a known sonomammography apparatus.
Figure 2:
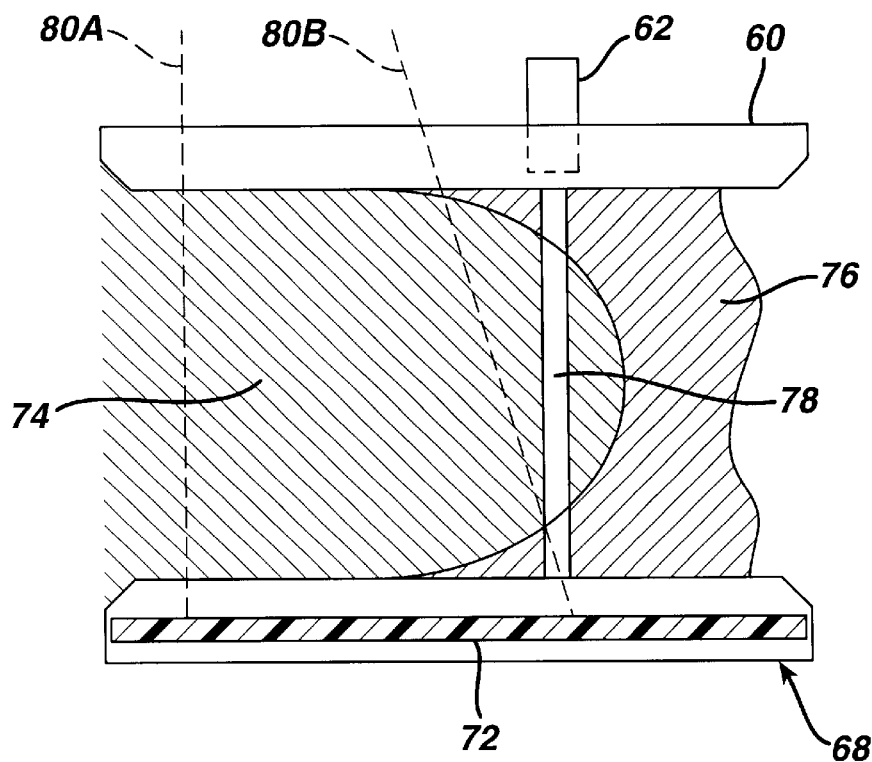
FIG. 2 is a schematic elevational view of part of the sonomammography apparatus shown in FIG. 1.

As shown in FIGS. 1 and 2, a known sonomammography apparatus 50 comprises a base 52, a vertical column 54, an X-ray tube 56 suspended from an arm 58, a upper compression plate 60, an ultrasound transducer 62 supported from a gantry 64, a gantry support 66, a combined lower compression plate, diffraction grid and film cassette assembly 68, and a biopsy needle guide 70. Vertical column 54 extends upward from and is supported by base 52. Vertical column 54 in turn supports arm 58, gantry support 66 and assembly 68. The vertical elevation of arm 58 relative to column 54 may be selectively and movably determined either manually or by using a motorized arrangement. X-ray film 72 (shown in FIG. 2) is disposed beneath the diffraction grid in the film cassette through a door in the end face of the film cassette.

As indicated in FIG. 2, when using the sonomammography apparatus to examine a patient's tissue, breast tissue 74 is compressed between upper compression plate 60 and assembly 68. Ultrasound transducer 62 is used to acquire acoustic data at multiple locations forming a grid of sample points. A beam of ultrasonic wave energy is transmitted into the tissue and focused at each grid point in each scan plane 78. Energy is reflected (echoed) by various structures within the tissue. The reflected energy is received, sampled, quantized and processed, as later described with reference to FIG. 3.

As shown in FIG. 2, an X-ray image of the breast is also obtained by exposing breast tissue 74 to an X-ray source (not shown) while tissue 74 is in the same position as when the ultrasonic data were being gathered. X-ray radiation, illustratively denoted by X-ray beams 80A and 80B, passes through compression plate 60, breast tissue 74 and assembly 68 to expose the X-ray film 72. The source of the X-rays is essentially a point source, so X-ray beams 80A and 80B are depicted in FIG. 2 as being not parallel. X-ray film 72 is then developed and the X-ray image is scanned and digitized for storage and processing.

While the mammography apparatus shown in FIGS. 1 and 2 also employs X-ray films, digital (i.e., filmless) X-ray systems employing solid-state X-ray detectors may alternatively be employed, or digitized X-ray film could be employed as film 72.

As shown in FIG. 1, upper compression plate 60 includes a gel pad 76 depending from the underside of the compression plate. Gel pad 76 may, for example, comprise a polyethylene bag filled with gel. Compression plate 60 may include fenestrations (not shown) for conducting biopsies of the patient's tissue. Alternatively, depending upon the composition of the gel material, gel pad 76 may be used without a polyethylene bag and may include a tacky or adherent surface to assist in positioning the breast. Gel pad 76 contacts the frontal area of the patient's breast 74, i.e., the nipple area, to ensure proper transmission of acoustic waves from ultrasound transducer 62 to the distal portion of breast tissue 74 with a minimum of impedance mismatch. As seen in FIG. 2, gel pad 76 conforms to the shape of the breast to minimize impedance mismatch and acoustic reflectance at the gel pad/breast interface. Accordingly, gel pad 76 may comprise an agar gelatin and water composition or other suitable rheostatic material.

The compression plate is preferably made of an acoustically transparent (sonolucent) and X-ray transparent (radiolucent) plastic material which is sufficiently rigid to serve as a compression plate. Preferably the compression plate has sufficient rigidity so that the local slope of the plate, under load, does not exceed one degree from the horizontal within the scan area.

Ultrasound transducer 62 comprises a one- or two-dimensional phased array of transducer elements, such as piezoelectric transducer elements. The transducer elements are activated at different times, in accordance with beamforming principles, to transmit a beam which is focused in a transmit focal zone inside the breast tissue. The beamforming time delays are varied from one transmit firing to the next to scan the ultrasound beam over the entire region of interest. The transmitted ultrasound beams must pass through compression plate 60 and into the breast tissue. Similarly, the echoes returned from the breast tissue to the transducer must again pass through the compression plate.

In order to form an in-focus image and avoid spherical aberration under these circumstances, the beamforming time delays must be computed to compensate for the effects of the increased speed of sound inside the compression plate. Before disclosing the method of correcting the beamforming delays to eliminate spherical aberration in accordance with a preferred embodiment of the invention, the structure and operation of an ultrasound imager beamformer will be described with reference to FIGS. 3 and 4.

An ultrasound imaging system in accordance with one preferred embodiment of the invention is generally depicted in FIG. 3. The system comprises a transducer array 2 including a plurality of separately driven transducer elements 4, each of which produces a burst of ultrasonic energy when energized by a pulsed waveform produced by a transmitter 8 and sent through a set of transmit/receive (T/R) switches 6 switched to a transmit state. The ultrasonic energy reflected back to transducer array 2 from the breast under study is converted to an electrical signal by each receiving transducer element 4 and applied separately to a receive beamformer 10 through T/R switches 6, which have now switched to a receive state. The T/R switches are typically diodes which protect the receive electronics from the high voltages generated by the transmit electronics. The transmit signal causes the diodes to shut off or limit the signal to the receiver. Transmitter 8 and receive beamformer 10 are operated under control of a host computer (i.e., master controller) 24. A complete scan is performed by acquiring a series of echoes after transmitter 8 has been gated ON momentarily to energize each transducer element 4 in the transmit aperture, and the subsequent echo signals in the form of low-level analog RF (radio frequency) signals produced by each transducer element 4 in response to reflected ultrasonic energy are applied to receive beamformer 10. The receive beamformer combines the separate echo signals from each transducer element to produce a single echo signal which is used to produce a line in an image on a display monitor 22.

The receive beamformer is responsible for analog-to-digital conversion and for receive beamforming. In baseband imaging systems, the beamsummed signal is supplied to a demodulator 12, which converts the beamsummed signal into baseband in-phase I and quadrature Q receive components. These I and Q acoustic data vectors from the demodulator 12 are sent to respective FIR (finite impulse response) filters 14 which are programmed with filter coefficients to pass a band of frequencies preferably centered at the center frequency of the transmit waveform or at a (sub)harmonic frequency thereof.

Vectors of filtered I and Q acoustic data are sent to a B-mode processor 16, which converts the I and Q acoustic data into a log-compressed version of the signal envelope. The B-mode function images the time-varying amplitude of the envelope of the signal as a gray scale. The envelope of a baseband signal is the magnitude of the vector which I and Q represent. The magnitude (i.e., intensity) of the signal is the square root of the sum of the squares of the orthogonal components, i.e., $(I^2+Q^2)^{1/2}$.

The B-mode intensity data are provided to a scan converter 18 comprising a B-mode acoustic line memory 17 followed by an X-Y display memory 19. The acoustic line memory accepts the processed vectors of B-mode intensity data and interpolates where necessary, and also performs a coordinate transformation of the B-mode intensity data from polar coordinate (R–θ) sector format or Cartesian coordinate linear format to appropriately scaled Cartesian coordinate display pixel intensity data, which are stored in the X-Y display memory.

The scan-converted frames are passed to a video processor 20, which converts the pixel intensity data to the video frame rate and then maps the pixel intensity data to a gray-scale mapping for video display. A conventional ultrasound imaging system typically employs a variety of gray maps, which are simple transfer functions of the raw intensity data to display gray-scale levels. The gray-scale image frames are sent to display monitor 22 for display.

The B-mode images displayed by monitor 22 are produced from an image frame of data in which each datum represents intensity or brightness of a respective pixel in the display. An image frame may, e.g., comprise a 400×500 data array in which each display pixel intensity datum is an 8-bit binary number that indicates pixel brightness. Each pixel has an intensity value which is a function of the backscatter from a respective sample volume in response to interrogating ultrasonic pulses and the gray map employed. The displayed image represents the tissue and/or blood flow in a plane through the breast being imaged.

System control is centered in a host computer 24, which accepts operator inputs through an operator interface 26 (e.g., a control panel) and in turn controls the various subsystems. Host computer 24 performs system level control functions. A system control bus (not shown) provides the interface from the host computer to the subsystems.

Figure 4:
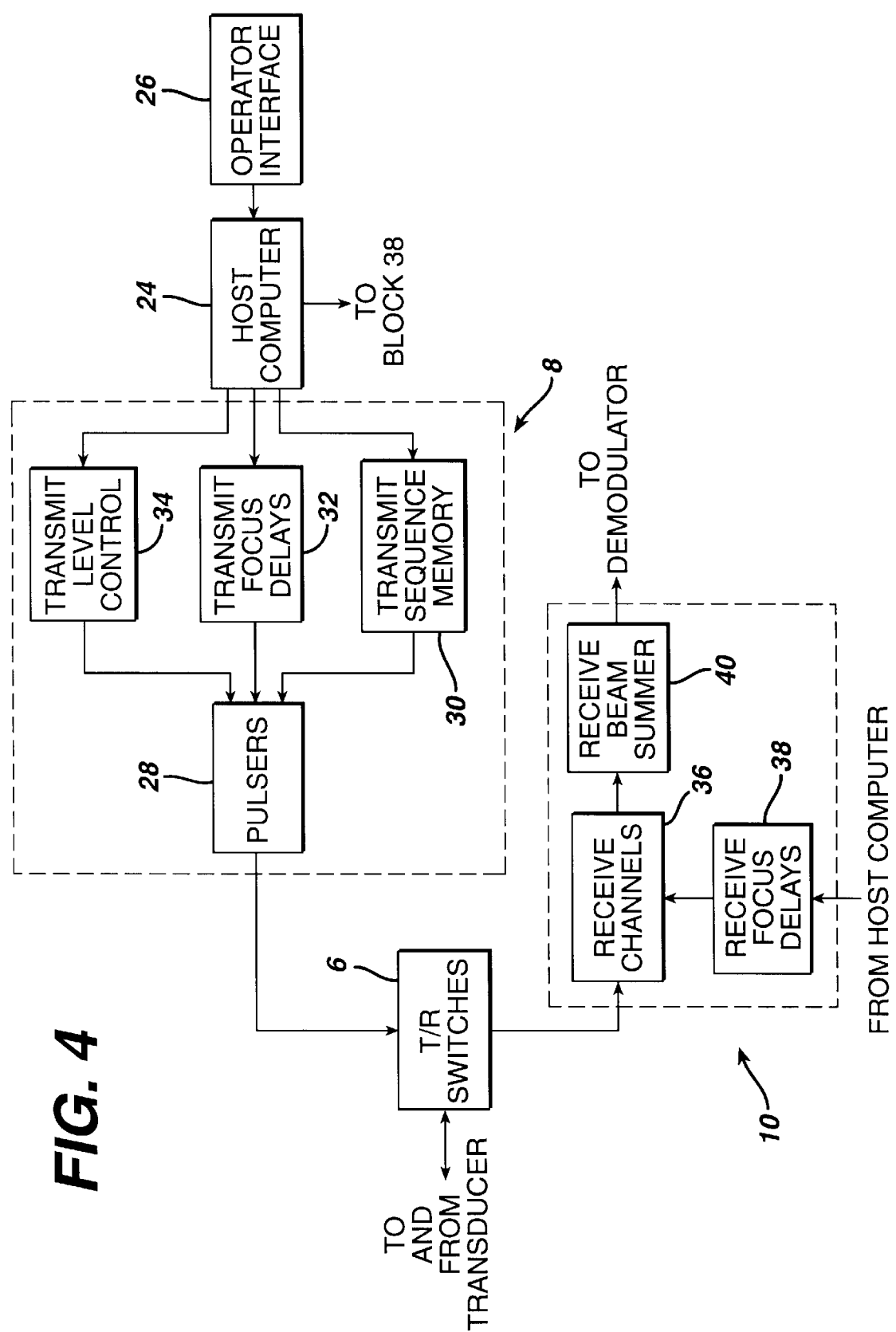
FIG. 4 is a block diagram showing in greater detail the transmitter and receiver of the system shown in FIG. 3.

In accordance with a preferred embodiment of the invention as shown in FIG. 4, transmit beamforming is implemented by programming a digital transmit sequence memory 30. Each transducer element in the transmit aperture is driven by a pulse waveform supplied from a respective pulser 28 in response to a respective transmit sequence provided to that pulser from transmit sequence memory 30. The frequency and length of each pulse waveform is determined by the respective transmit sequence. For example, if pulser 28 is discrete and bipolar, +1 and −1 elements of a transmit sequence are transformed into pulses of opposite phase by the pulser, while 0 elements correspond to no pulse. The duty cycle or pulse width is proportional to the number of consecutive +1's or −1's in the transmit sequence.

Under the direction of host computer 24, transmitter 8 drives the transducer array such that the ultrasonic energy is transmitted as a directed focused beam. To accomplish focusing, respective time delays are imparted to pursers 28 by a transmit focus delays subsystem 32, while respective pulse amplitudes are set by a transmit level control subsystem 34. Host computer 24 determines the conditions under which the acoustic pulses will be transmitted. With this information, the transmit focus delays and transmit level control subsystems respectively determine the timing and the amplitude of each of the transmit pulses to be generated by pursers 28, while the frequency and length of the transmit pulses are determined by the transmit sequences. In particular, the time delays used by the transmit focus delays subsystem for transmit beamforming originate in the host computer. By appropriately adjusting the transmit focus time delays, the ultrasonic beam for each firing can be focused at a desired transmit focal zone position.

After each transmission, T/R switches 6 are switched to receive mode to pass the returning echoes backscattered from the object being scanned. These return signals are fed to respective receive channels 36 of the receive beamformer. The receive beamformer tracks echoes under the direction of host computer 24. The receive beamformer imparts the proper receive focus time delays (subsystem 38) to the received RF echo signals. In particular, the receive focus time delays 38 for receive beamforming originate in the host computer. Beamsummer 40 sums the RF echo signals from all receive channels to provide an echo signal which accurately represents the total ultrasonic energy reflected from a succession of ranges. Multiple images, each from a particular transmit focal zone, may be combined to produce a composite image that approximates dynamic transmit focus.

The fundamental principle of time delay beam-forming consists of collecting echoes at the elements and then time shifting these echoes so that they line up with the echoes arriving at the phase center of the beam, which in this instance is at the physical center of the array. In the following discussion, the compression plate is planar, having mutually parallel upper and lower surfaces, and made of acoustically transmissive material having a speed of sound different than that of breast tissue.

A procedure is disclosed for correcting the focus of a phased array ultrasound imaging device when it is imaging through the compression plate of an X-ray mammography unit. This correction allows acquisition of an in-focus ultrasound image obtained under the same conditions as an X-ray mammography image. Since the two images are formed from a source at the same location under the same conditions, they can be registered, and their information can be compared on a point-by-point basis.

Figure 5:
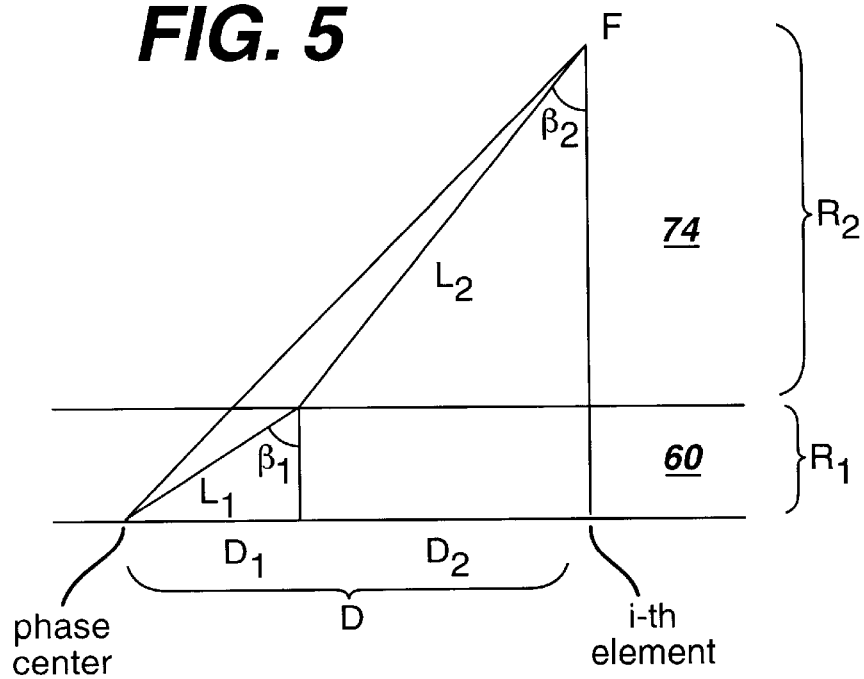
FIG. 5 is a schematic illustration of the basic geometry of time delay when an acoustic medium has two layers having different thicknesses and different speeds of sound.

In order to eliminate spherical aberration caused by the intervening compression plate, the beamforming delays applied to the array elements of the transducer must be corrected. These delays are computed to compensate for the time-of-flight from the i-th array element to the focal point, under the assumption of a uniform medium with a speed of sound of 1,540 meters/sec. In order to obtain the correct delays, the time-of-flight along the refracted ray path joining the center of each array element to the focal point must be computed. A two-dimensional version of the applicable geometry is depicted in FIG. 5. The three-dimensional geometry (not shown) is a trivial extension.

FIG. 5 depicts a situation in which the acoustic medium has two layers, the lower one (i.e., compression plate 60) having thickness $R_1$ and speed of sound $c_1$, and the upper one (i.e., breast tissue 74) having thickness $R_2$ and speed of sound $c_2$. The point marked F is the focal point, and D is the distance from the i-th array element to the phase center of the aperture. The time of flight T along the refracted path $L_1$, $L_2$ is:

$$T = \frac{L_1}{c_1} + \frac{L_2}{c_2} \tag{1}$$

Therefore the problem is to solve for $L_1$ and $L_2$, given $R_1$, $c_1$, $R_2$ and $c_2$. The angles $\beta_1$ and $\beta_2$ are related by Snell's law as follows:

$$\beta_1 = \arcsin\left[\frac{c_1}{c_2}\sin(\beta_2)\right] \tag{2}$$

and given $\beta_1$ and $\beta_2$, $L_1$ and $L_2$ can be computed as $$L_i = \frac{R_i}{\cos(\beta_i)} \tag{3}$$

so that $$T = \frac{R_1}{c_1\cos(\beta_1)} + \frac{R_2}{c_2\cos(\beta_2)}. \tag{4}$$

Then the angle $\beta_2$ can be computed using the following expression:

$$= R_1 \tan\left[\arcsin\left(\frac{c_1}{c_2}\sin(\beta_2)\right)\right] + R_2\tan(\beta_2).. \tag{5}$$

Equation (5) can be solved numerically for $\beta_2$, which can then be used in Snell's law to compute $\beta_1$. The two angles are then substituted into Eq. (4) to compute the time-of-flight. The beamforming time delays for each transmit focal position can be derived from the difference in the time-of-flight for each transducer element relative to the time-of-flight to the phase center of the array.

Host computer 24, shown in FIG. 4, may compute transmit and receive time delays as a function of compression plate thickness and speed of ultrasound propagation supplied by the operator via operator interface 26. The computed transmit time delays are then sent to transmit focus delays subsystem 32 in transmitter 8, while the computed receive time delays are sent to receive focus delays subsystem 38 in receiver 10. Alternatively, sets of time delays may be precalculated and stored in computer memory, each time delay set corresponding to a different compression plate having a different set of compression plate thickness and speed of ultrasound propagation values. In response to the compression plate thickness and speed of ultrasound propagation values supplied by the operator, the host computer retrieves the corresponding set of time delays from memory and sends them to the transmitter and receiver.

While only certain preferred features of the invention have been illustrated and described, many modifications and changes will occur to those skilled in the art. It is, therefore, to be understood that the appended claims are intended to cover all such modifications and changes as fall within the true spirit of the invention.

What is claimed is:

1. A system for transmitting a beam of ultrasound wave energy into a medium, comprising:

a transducer array including a multiplicity of transducer elements, said transducer array having a phase center;

an acoustically transmissive mammography compression plate arranged between said transducer array and the medium; and a transmitter programmed to drive said transducer elements with respective excitation waveforms during a transmit firing, said excitation waveforms having respective predetermined time delays such that ultrasound waves produced by said transducer elements in response to said excitation waveforms combine to form a transmit beam which is focused at a transmit focal zone position located at a predetermined range and a predetermined angle relative to said phase center of said transducer array, wherein said predetermined time delays are determined based on said transmit beam being refracted by said mammography compression plate before reaching said transmit focal zone position.

2. The system as recited in claim 1, wherein said transmitter comprises a multiplicity of pulsers respectively coupled to said multiplicity of transducer elements for providing said excitation waveforms to said transducer elements, and programmable transmit focus delays control means for controlling the time delays applied to said excitation waveforms.

3. The system as recited in claim 2, further comprising an operator interface, and means for storing a plurality of sets of time delays and for programming said transmit focus delays control means with a selected set of time delays in response to a predetermined operator input at said operator interface.

4. A method for operating an array of transducer elements to transmit a beam of ultrasound wave energy into a medium, comprising the steps of:

placing an acoustically transmissive mammography compression plate between the array and the medium; and driving the transducer elements with respective excitation waveforms during a transmit firing, said excitation waveforms having respective predetermined time delays such that ultrasound waves produced by the transducer elements in response to said excitation waveforms combine to form a transmit beam which is focused at a transmit focal zone position located at a predetermined range and a predetermined angle relative to a phase center of the array, wherein said predetermined time delays are determined based on said transmit beam being refracted by the mammography compression plate before reaching said transmit focal zone position.

5. A system for transducing ultrasound wave energy received from a medium into an electrical signal, comprising:

a transducer array including a multiplicity of transducer elements arranged to transduce respective rays of ultrasound wave energy impinging thereon;

an acoustically transmissive mammography compression plate arranged between said transducer array and the medium; and a receive beamformer programmed to sum respective electrical signals received from said multiplicity of transducer elements in accordance with respective predetermined time delays applied to said electrical signals, said predetermined time delays being determined based on refraction by said mammography compression plate of waves of ultrasound wave energy from a point source in a field of view of said transducer array so that summation produces a net electrical signal which is indicative of ultrasound wave energy emanating from said point source.

6. The system as recited in claim 5, wherein said receive beamformer comprises a multiplicity of receive channels respectively coupled to said multiplicity of transducer elements, and programmable receive focus delays control means for controlling the time delays applied to said electrical signals.

7. The system as recited in claim 6, further comprising an operator interface, and means for storing a plurality of sets of time delays and for programming said receive focus delays control means with a selected set of time delays in response to a predetermined operator input at said operator interface.

8. A method for transducing ultrasound wave energy from a medium into electrical signals representing a receive beam, comprising the steps of:

placing an acoustically transmissive mammography compression plate between an array of ultrasound transducing elements and the medium;

transducing waves of ultrasound wave energy impinging on the transducing elements into respective electrical signals;

applying respective predetermined time delays to said electrical signals, said predetermined time delays being determined based on refraction by the compression plate of ultrasound waves arriving from a point in a field of view of the array so that summation will produce a net electrical signal indicative of ultrasound wave energy arriving from said point; and summing said time-delayed electrical signals.

9. An imaging system comprising:

an acoustically transmissive mammography com-pression plate;

a transducer array arranged on one side of said compression plate, said array including a multiplicity of piezoelectric transducer elements directed to transmit ultrasound wave energy into said compression plate;

a transmitter programmed to drive said transducer elements with respective excitation waveforms during a transmit firing, said excitation waveforms having respective predetermined transmit time delays such that ultrasound waves produced by said transducer elements in response to said excitation waveforms combine to form a transmit beam which is focused at a transmit focal zone position located on the other side of said compression plate, said predetermined transmit time delays being determined based on said transmit beam being refracted by said compression plate before reaching said transmit focal zone position;

a receive beamformer programmed to sum respective receive signals received from said multiplicity of transducer elements in accordance with respective predetermined receive time delays applied to said receive signals, said predetermined receive time delays being determined based on refraction by said compression plate of echo signals propagating from said transmit focal zone position to said transducer array so that summation will produce a net receive signal indicative of ultrasound wave energy emanating from said transmit focal zone position;

a processor for deriving an image signal from said net receive signal; and a display device for displaying an image having an image portion which is a function of said image signal.

10. The system as recited in claim 9, wherein said transmitter comprises a multiplicity of pulsers respectively coupled to said multiplicity of transducer elements, and programmable transmit focus delays control means for controlling the transmit time delays applied to said excitation waveforms produced by said pursers.

11. The system as recited in claim 10, wherein said receive beamformer comprises a multiplicity of receive channels respectively coupled to said multiplicity of transducer elements, and programmable receive focus delays control means for controlling the receive time delays applied to said receive signals.

12. The system as recited in claim 9, further comprising an operator interface, and means for storing a plurality of sets of transmit and receive time delays and for programming said transmit and receive focus delays control means with a selected set of transmit and receive time delays, respectively, in response to a predetermined operator input at said operator interface.

13. A method for programming an imaging system, comprising the steps of:

calculating respective distances traveled by respective rays to be transmitted from elements of an ultrasound transducer, refracted by an acoustically transmissive mammography compression plate, and focused in a desired transmit focal zone;

calculating respective beamforming time delays as a function of said respective distances; and loading said respective beamforming time delays into system memory, wherein the calculated respective beamforming time delays are a function of the speed of sound and thickness of said compression plate.

14. An imaging system comprising:

an acoustically transmissive mammography compression plate;

a transducer array arranged on one side of said compression plate, said array comprising a multiplicity of piezoelectric transducer elements directed to transmit ultrasound wave energy into said compression plate;

a display monitor for displaying an image having an image portion which is a function of an image signal; and a computer programmed to perform the steps of:
  (a) driving transducer elements forming a transmit aperture with excitation waveforms in accordance with a set of transmit time delays to form a beam focused at a transmit focal zone position located on the other side of said compression plate, said transmit time delays being determined based on said transmit beam being refracted by said compression plate before reaching said transmit focal zone position;
  (b) forming a beamsummed signal from a set of receive signals received from transducer elements forming a receive aperture in accordance with a set of receive time delays respectively applied to said receive signals, said receive time delays being determined based on refraction by said compression plate of ultrasound echo signals propagating from said transmit focal zone position to said transducer array;
  (c) processing said beamsummed signal to form an image signal; and
  (d) providing said image signal to said display monitor.

15. An imaging system comprising:

an acoustically transmissive mammography compression plate;

a transducer array arranged on one side of said compression plate, said array comprising a multiplicity of piezoelectric transducer elements directed to transmit ultrasound wave energy into said compression plate;

a transmitter beamformer coupled to said transducer array in a transmit mode;

a receive beamformer coupled to said transducer array in a receive mode;

a controller programmed and connected to perform the steps of:
  (a) providing said transmitter with a set of transmit time delays to cause said transducer array to transmit a beam focused at a transmit focal zone position located on the other side of said compression plate, said transmit time delays being determined based on said transmit beam being refracted by said compression plate before reaching said transmit focal zone position; and
  (b) providing said receive beamformer with a set of receive time delays to cause said receive beamformer to form a beamsummed receive signal from a set of receive signals transduced by said transducer array, said receive time delays being determined based on refraction by said compression plate of echo signals propagating from said transmit focal zone position to said transducer array;

detector means for forming an image signal derived from said beamsummed receive signal; and a display subsystem for displaying an image having an image portion which is a function of said image signal.

16. A method for imaging biological tissue of a breast positioned beneath an acoustically transmissive mammography compression plate, comprising the steps of:

placing an array of transducer elements against said breast;

transmitting a transmit beam from said array using a set of transmit time delays, said transmit beam being focused in a transmit focal zone, and said transmit time delays being determined based on said transmit beam being refracted by said compression plate before reaching said transmit focal zone;

transducing ultrasound waves returned to said array from said transmit focal zone to form a respective electrical receive signal for each of said transducer elements;

time delaying the receive signals with a set of receive beamforming time delays, said receive beam-forming time delays being determined based on refraction by said compression plate of returning ultrasound waves so that summation of said receive signals will produce a beamsummed signal indicative of the magnitude of ultrasound wave energy returned to said array from said transmit focal zone subsequent to transmission of said transmit beam;

summing the time-delayed receive signals to form said beamsummed signal;

processing said beamsummed signal to form an image signal; and displaying an image having an image portion which is a function of said image signal.

17. An imaging system comprising:

an acoustically transmissive mammography compression plate;

a source of X-rays located on one side of said compression plate and directed to transmit X-rays through said compression plate;

an X-ray detector located on the other side of said compression plate;

an ultrasonic transducer array movably located on said one side of said compression plate, said array comprising a multiplicity of piezoelectric transducer elements directed to transmit ultrasound wave energy through said compression plate;

a transmitter coupled to said tranducer array;

a receive beamformer coupled to said transducer array;

a controller coupled to provide said transmitter in a transmit mode with a set of transmit time delays that cause said transducer array to transmit a beam focused at a transmit focal zone position located on said other side of said compression plate, said transmit time delays being determined based on said transmit beam being refracted by said compression plate before reaching said transmit focal zone position, said controller further coupled to provide said receive beamformer in a receive mode with a set of receive time delays to cause said receive beamformer to form a beamsummed receive signal from a set of receive signals transduced by said transducer array, said receive time delays being determined based on refraction by said compression plate of echo signals propagating from said transmit focal zone position to said transducer array;

a signal processor for forming an image signal derived from said beamsummed receive signal; and a display subsystem for displaying an image having an image portion which is a function of said image signal.

18. An imaging system comprising:

an acoustically transmissive mammography compression plate;

a source of X-rays located on one side of said compression plate and directed to transmit X-rays through said compression plate;

an X-ray detector located on the other side of said compression plate;

an ultrasonic transducer array movably located on said one side of said compression plate, said array comprising a multiplicity of transducer elements directed to transmit ultrasound wave energy through said compression plate;

a transmitter coupled to said transducer array;

a receive beamformer coupled to said transducer array;

said transmitter and said receive beamformer being adapted to be programmed with transmit and receive time delays, respectively, which are adjusted to compensate for refraction produced by said compression plate, said receive beamformer being adapted to form a respective receive beam for each transmit beam in a scanning plane;

a data processor for forming image signals which are a function of said receive beams; and a display subsystem for displaying an image derived from said image signals.

19. The imaging system of claim 18 wherein said X-ray detector comprises X-ray film.

20. The imaging system of claim 18 wherein said X-ray detector comprises a solid-state X-ray detector.

* * * * *